United States Patent
Furukawa et al.

(10) Patent No.: US 7,189,855 B2
(45) Date of Patent: Mar. 13, 2007

(54) PROCESS FOR PRODUCTION OF PHENOXY-SUBSTITUTED 2-PYRIDONE COMPOUNDS

(75) Inventors: Takashi Furukawa, Chiba (JP); Noritada Matsuo, Amagasaki (JP); Yoshitomo Tohyama, Ashiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 314 days.

(21) Appl. No.: 10/513,373

(22) PCT Filed: Jun. 20, 2003

(86) PCT No.: PCT/JP03/07843

§ 371 (c)(1),
(2), (4) Date: Nov. 3, 2004

(87) PCT Pub. No.: WO04/000812

PCT Pub. Date: Dec. 31, 2003

(65) Prior Publication Data

US 2005/0154210 A1    Jul. 14, 2005

(30) Foreign Application Priority Data

Jun. 25, 2002 (JP) .............................. 2002-184105

(51) Int. Cl.
*C07D 213/64* (2006.01)
(52) U.S. Cl. ..................................... 546/296
(58) Field of Classification Search ................. 546/296
See application file for complete search history.

(56) References Cited

U.S. PATENT DOCUMENTS 6,537,948 B1   3/2003   Tohyama et al.

FOREIGN PATENT DOCUMENTS

| JP | 2000-119252 A | 4/2000 |
|----|---------------|--------|
| JP | 2003-48886 A  | 2/2003 |

OTHER PUBLICATIONS

Bonsall, C., et al., "8-Azachromones", *J. Chem. Soc.* (C), pp. 1836-1839 (1967).
Kato, T., et al., "Synthesis of Methylpyridine Deriviatives XXXIV. Condensation of Acetoacetamide with Ketones to form Pyridone Derivatives", *Chem. Pharm. Bull.*, vol. 28, No. 7, pp. 2244-2247 (1980).

*Primary Examiner*—Zinna N. Davis
(74) *Attorney, Agent, or Firm*—Akin Gump Strauss Hauer & Feld LLP

(57) ABSTRACT

3-Phenoxy-2-pyridone compound can be produced by making the amide compound of the formula (1):

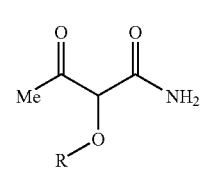

(1)

wherein R is optionally substituted phenyl;
react with a malonoaldehyde derivative such as 3-alkoxypropenal and the like in the presence of a protonic acid.

5 Claims, No Drawings

1

PROCESS FOR PRODUCTION OF PHENOXY-SUBSTITUTED 2-PYRIDONE COMPOUNDS

CROSS-REFERENCE TO RELATED APPLICATION

This application is a Section 371 of International Application No. PCT/JP03/007843, filed Jun. 20, 2003, which was published in the Japanese language on Dec. 31, 2003, under International Publication No. WO 2004/000812 A1 the disclosure of which is incorporated herein by reference.

TECHNICAL FIELD

The present invention relates to a process for producing phenoxy-substituted 2-pyridone compounds, which is useful for intermediates of medicinal and agricultural product, especially herbicidal compound.

BACKGROUND ART

It is known that 2-pyridone compounds can be produced by making 3-oxobutanamide react with a various kind of ketone compound. Specifically, 4,6-dimethyl-2-pyridone is obtained by making 3-oxobutanamide react with acetone in the presence of polyphosphoric acid; 3-acetyl-4,6-dimethyl-2-pyridone is obtained by making 3-oxobutanamide react with pentan-2,4-dione in the presence of hydrogen chloride or polyphosphoric acid; and 5-ethoxycarbonyl-4,6-dimethyl-2-pyridone is obtained by making 3-oxobutanamide react with ethyl acetoacetate in the presence of polyphosphoric acid (Chem. Pharm. Bull. 28(7) 2244–2247 (1980). J. Chem. Soc. (C), 1967, 1836–1839).

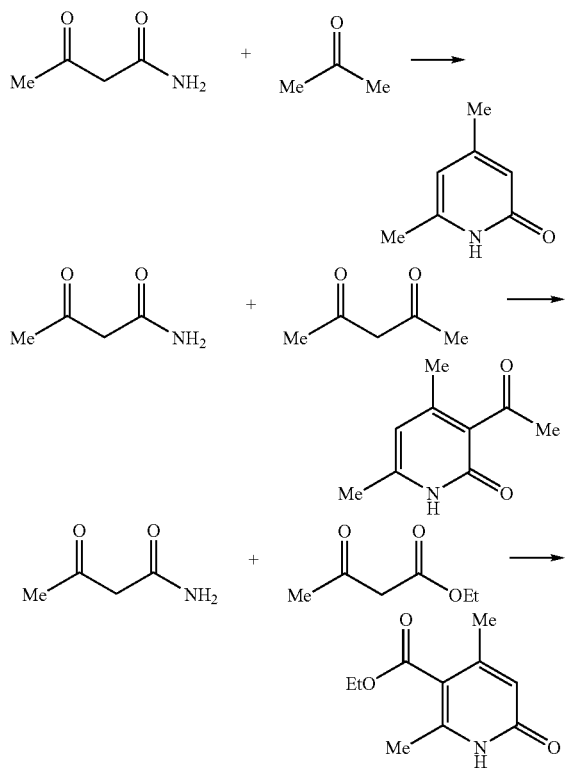

DISCLOSURE OF INVENTION

The present inventors have intensively studied a process for producing a 2-pyridone compound substituted at 3-position with optionally substituted phenoxy, that is useful for intermediates of medicinal and agricultural product, especially herbicidal compound. As a result, the present inventors was found out that 3-phenoxy-2-pyridone compound only substituted at 3-position can be obtained by 2-phenoxy-3-oxobutanamide compound, in which the phenoxy can be substituted, react with a certain of malonaldehyde derivative or malonaldehyde, thereby completing the present invention.

The present invention provides a process (hereinafter, referred to as the present process) for producing a pyridone compound of the formula (2) (hereinafter, referred to as the present pyridone compound):

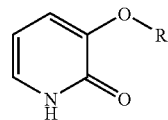
(2)

wherein R is defined below;

which comprises making an amide compound of the formula (1) (hereinafter, referred to as the present amide compound):

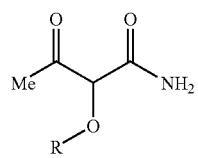
(1)

wherein R represents an optionally substituted phenyl;

react with at least one compound (hereinafter, referred to as the present malonaldehyde derivative) selected from the group consisting of 3-alkoxypropenal of the formula (3), 3,3-dialkoxypropanal of the formula (4), 1,3,3-trialkoxy-1-propene of the formula (5), 1,1,3,3-tetraalkoxypropane of the formula (6), and malonaldehyde:

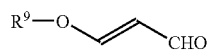
(3)

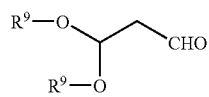
(4)

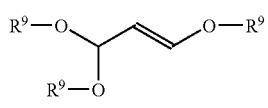
(5)

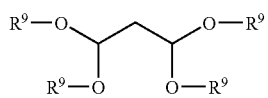
(6)

wherein $R^9$ represents alkyl (e.g. C1–C3 alkyl such as methoxy, ethoxy and the like);

in the presence of a protonic acid.

Furthermore, the present invention also provides a process for producing a pyridone compound of the formula (B):

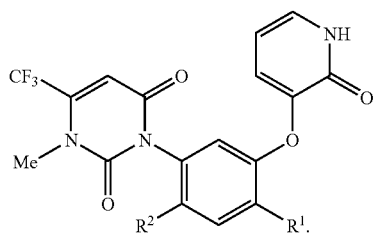

(B)

wherein $R^1$ and $R^2$ are defined below;

by using an amide compound of the formula (A):

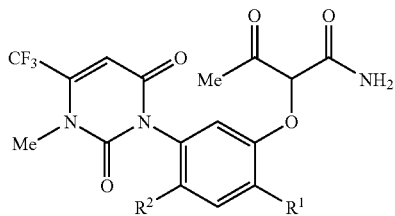

(A)

wherein $R^1$ represents a halogen atom or nitro, and $R^2$ represents a hydrogen atom or halogen atom;

as the present amide compound.

The substituent on the optionally substituted phenoxy of the present amide compound, which is a starting compound of the present process, and the present pyridone compound includes, for example, a halogen atom (e.g. a fluorine atom, chlorine atom, bromine atom and the like); alkyl (e.g. C1–C4 alkyl such as methyl, ethyl, propyl, isopropyl and the like); alkoxy (e.g. C1–C4 alkoxy such as methoxy, ethoxy, propoxy, isopropoxy and the like); haloalkyl (e.g. trifluoromethyl, pentafluoroethyl); nitro; cyano; and 5–6 membered heterocyclic radical (e.g. 1,2,3,6-tetrahydro-2,6-dioxopyrimidin-1-yl, 1,6-dihydro-6-oxopyridazin-1-yl and he like). The optionally substituted phenoxy includes, for example, phenoxy and he phenoxy shown with the scheme:

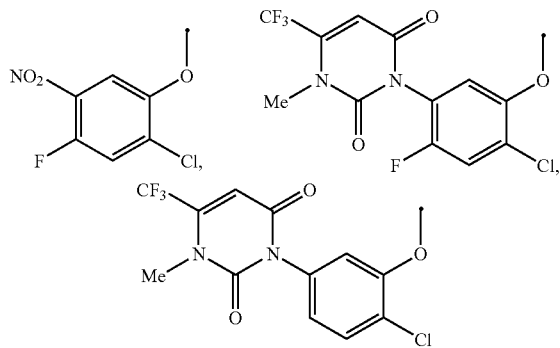

wherein $R^1$ and $R^2$ is defined above.

The present amide compound includes, for example, the compound shown with the scheme:

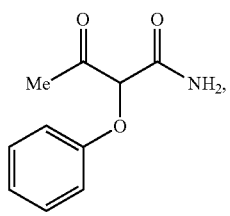

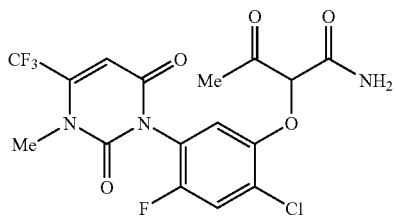

The present malonaldehyde derivative means malonaldehyde, or formal condensation products of malonaldehyde and alcohol, which is specifically at least one malonaldehyde derivative selected from the group consisting of 3-alkoxypropenal of the formula (3), 3,3-dialkoxypropanal of the formula (4), 1,3,3-trialkoxy-1-propene of the formula (5), 1,1,3,3-tetraalkoxypropane of the formula (6). 3-Alkoxypropenal of the formula (3) includes, for example, 3-methoxypropenal and 3-ethoxypropenal. 3,3-Dialkoxypropanal of the formula (4) includes, for example, 3,3-dimethoxypropanal and 3,3-diethoxypropanal. 1,3,3-Trialkoxy-1-propene of the formula (5) includes, for example, 1,3,3-trimethoxy-1-propene and 1,3,3-triethoxy-1-propene. 1,1,3,3-Tetraalkoxypropane of the formula (6) includes, for example, 1,1,3,3-tetramethoxypropane and 1,1,3,3-tetraethoxypropane.

In the present process, 1,1,3,3-tetraalkoxypropane of the formula (6) is preferable compound as the malonaldehyde derivative, considering the factor of obtainability and the like.

The protonic acid to be used in the present process means a substance having a strong tendency to donate a proton, namely in the definition of Brønsted acids and bases theory based on donating and accepting of proton. Specifically, the protonic acid includes hydrogen halides (e.g. hydrogen chloride, hydrogen bromide and the like), phosphoric acid, polyphosphoric acid, sulfuric acid, trihaloacetic acid (e.g. trichloroacetic acid, trifluoroacetic acid and the like), sulfonic acid (e.g. chlorosulfonic acid, methanesulfonic acid, p-toluenesulfonic acid, trifluoromethanesulfonic acid and the like) and the mixture thereof; preferably protonic acids having 2.5 or lower pKa, which is an acid dissociation constant in water.

The reaction of the present process may be carried out in a solvent. The solvent to be used includes, for example, aromatic hydrocarbons such as toluene, xylene and the like; halogenated aromatic hydrocarbons such as chlorobenzene, dichlorobenzene, benzotrifluoride and the like; halogenated aliphatic hydrocarbons such as chloroform, 1,2-dichloroethane and the like; alcohols such as hexafluoroisopropanol and the like; and the mixture thereof.

In the reaction, 1 to 10 moles of the present malonaldehyde derivative and catalytic to excess amount (e.g. 0.1 to 1000 moles, preferably 1 to 10 moles) of the acid are usually used, relative to 1 mole of the present amide compound.

The reaction temperature of the reaction is usually in a range of 0 to 150° C., preferably 20 to 100° C., and the reaction time is usually in a range of 0.5 to 72 hours, yet they are changeable by an amount and species of the protonic acid to be used.

The reaction is carried out with adding the present amide compound and the present malonaldehyde derivative into the protonic acid or a medium diluted the proton acid with the above-mentioned solvent. In this case, it is allowed that all of the proton acid is used at once at starting reaction; and a part of the proton acid is used at starting reaction and a rest of the proton acid is added as according to progress of the reaction. The present amide compound and the present malonaldehyde may be added all at once into the protonic acid or a medium diluted the proton acid with the above-mentioned solvent; but preferably, the present amide compound and the present malonaldehyde should be added progressively as according to the progress of the reaction.

The progress of the reaction can monitored, for example, by sampling a part of the reaction mixture and subjecting it to chromatography (e.g. thin layer chromatography, high performance liquid chromatography and the like) to analyze a remaining amount of the amide compound of the formula (1) in the reaction mixture.

The present pyridone compound can be isolated from the reaction mixture after completion of the reaction by the following procedure:

1) Diluting the reaction mixture after completion of the reaction with a hydrophobic organic solvent; washing it with saturated sodium chloride aqueous solution, saturated sodium bicarbonate aqueous solution or the like; drying the obtained organic layer; and concentrating it to remove the solvent completely.
2) Diluting the reaction mixture after completion of the reaction with a hydrophobic organic solvent; washing it with saturated sodium chloride aqueous solution, saturated sodium bicarbonate aqueous solution or the like; partially concentrating it at 80 to 120° C. and cooling; and filtering off and drying the generated solid.
3) Partially concentrating the reaction mixture after completion of the reaction; pouring it a mixture of water and a hydrophilic organic solvent at any ratio; and filtering off and drying the generated solid.
4) Poring the reaction mixture after completion of the reaction into water; adjusting pH of the water layer to about neutral; removing the organic solvent with azeotropic distillation; and drying the generated solid.

The hydrophobic organic solvent to be used in the post-treatment procedure includes, for example, esters such as ethyl acetate and the like; halogenated aliphatic hydrocarbons such as chloroform and the like; halogenated aromatic hydrocarbons such as chlorobenzene, dichlorobenzene, benzotrifluoride and the like; ketones such as methyl isobutyl ketone and the like; and the mixture thereof. The hydrophilic organic solvent includes, alcohols such as methanol, ethanol, isopropyl alcohol, t-butyl alcohol and the like.

The isolated present pyridone compound can be purified by chromatography, recrystallization, washing with a poor solvent, and the like.

The present amide compound to be used in the present process can be produced, for example, by making the phenol compound of the formula (7) react with the amide compound of the formula (8) (e.g. 2-chloro-3-oxobutanamide):

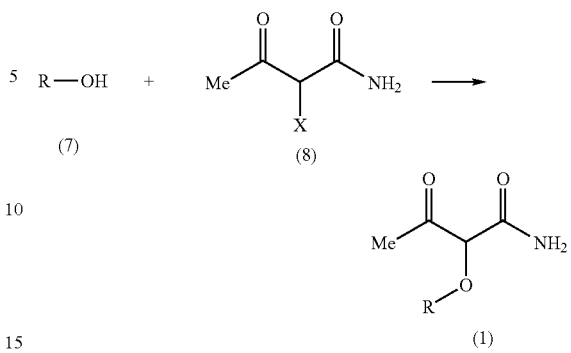

wherein X represents a halogen atom, and R is defined below.

The reaction is usually carried out in the presence of base in a solvent. The solvent to be used includes, for example, aromatic hydrocarbons such as toluene, xylene and the like; acid amides such as N,N-dimethylformamide and the like. The base to be used includes, for example, inorganic bases such as sodium carbonate, potassium carbonate and the like; tertiary amines such as triethylamine, tributylamine and the like.

In the reaction, 1 to 1.5 mole of the amide compound of the formula (8) and 1 to 3 mole of the base are usually used, relative to 1 mole of the phenol compound of the formula (7).

The reaction temperature of the reaction is usually in a range of 20 to 150° C., and the reaction time is usually in a range of 0.5 to 24 hours.

The present amide compound can be isolated from the reaction mixture after completion of the reaction, for example, by diluting the reaction mixture with organic solvent, washing it with saturated sodium chloride aqueous solution, saturated sodium bicarbonate aqueous solution or the like, drying and concentrating the obtained organic layer. The isolated amide compound can be purified by chromatography, recrystallization and the like.

The present malonaldehyde derivative to be used in the present process is known compound itself, or can be produced according to the method described in a public document.

As the public document, the following documents are exemplified.

Japanese Publication of unexamined application S52-97905, for 3-alkoxypropenal of the formula (3);

J. Chem. Soc., Chem. Commun., (20) 1421–1422 (1991), for 3,3-dialkoxypropanal of the formula (4);

Tetrahedron Lett., 29 (29) 3597–3598 (1988), for 1,3,3-trialkoxy-1-propene of the formula (5);

J. Org. Chem. 53 (13) 2920–2925 (1988), for 1,1,3,3-tetraalkoxypropane of the formula (6);

J. Org. Chem., 50 3585–3592 (1985), for malonaldehyde.

The present pyridone compound produced by the present process is useful for intermediates of medicinal and agricultural product. For example, the pyridine compound of the formula (D) can be produced by making the compound of the formula (B) react with the diazo acetic acid ester compound of the formula (C) in the presence of rhodium (II) salt, boron trifluoride, p-toluenesulfonic acid or the like. The obtained pyridine compound of the formula (D) is useful for an active ingredient of herbicidal composition (European patent application publication EP1122244 A1).

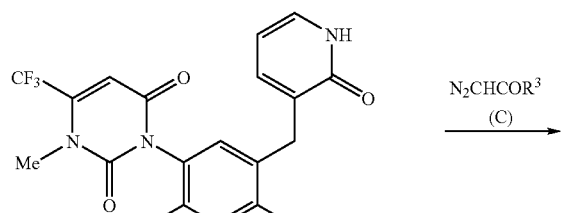

(B)

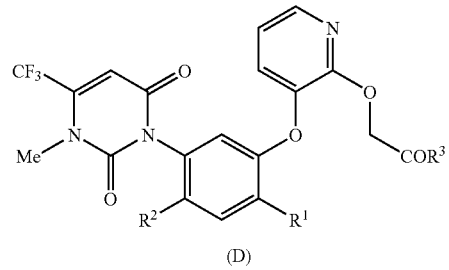

(D)

wherein R³ represents C1–C6 alkoxy.

In the case of the reaction in the presence of rhodium (II) salt; the reaction is usually carried out in a solvent, the reaction temperature is in a range of 60 to 120° C., and the reaction time is in a range of instant to 72 hours. The solvent to be used includes, for example, halogenated hydrocarbons such as 1,2-dichloroethane and the like. Usually, the amount of diazoacetate compound of the formula (C) is 0.5 to 2 moles, and the amount of the rhodium (II) salt is 0.01 to 0.05, relative to 1 mole of the compound of the formula (B). These amount can be changeable according to the reaction condition. The rhodium (II) salt to be used includes, for example, rhodium (II) trifluoroacetate dimer.

After completion of the reaction, the pyridine compound of the formula (D) can be isolated from the reaction mixture by subjecting the reaction mixture to the post-treatment such as filtering the reaction mixture and concentrating the filtrate; and diluting the reaction mixture with an organic solvent and separated from sodium bicarbonate aqueous solution, drying and concentrating the obtained organic layer; and the like. The isolated pyridine compound can be purified by chromatography and the like.

The present invention will be further illustrating by the following production examples and the like; however the present invention is not limited to these examples. Additionally, "part" means a part by weight in the following description.

PRODUCTION EXAMPLE 1

Under nitrogen atmosphere, 57 mg of 3-oxo-2-phenoxybutanamide and 49 mg of 1,1,3,3-tetramethoxypropane were added into 2 ml of 25% hydrogen bromide solution in acetic acid, and stirred at 50° C. for 2.5 hours and at 100° C. for 2 hours. In the reaction mixture were added 80 ml of ethyl acetate and 30 ml of saturated sodium chloride aqueous solution, and the mixture was separated.

The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 36 mg of 3-phenoxy-2-pyridone.

¹H-NMR (395.75M Hz, CDCl₃) δ (ppm): 6.18 (t, J=6.9 Hz, 1H), 6.92 (dd, J=7.5, 1.7 Hz, 1H), 7.08 (brd, J=7.8 Hz, 2H), 7.15 (brt, J=7.5 Hz, 1H), 7.19 (dd, J=6.7, 1.7 Hz, 1H), 7.36 (brt, J=7.5 Hz, 2H), 13.7 (brs, 1H)

PRODUCTION EXAMPLE 2

Under nitrogen atmosphere, 108 mg of the amide compound of the formula (F):

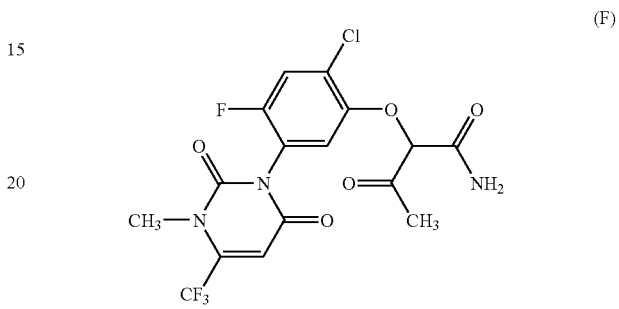

and 53 mg of 1,1,3,3-tetramethoxypropane were added into 2 ml of 85% phosphoric acid aqueous solution, and stirred at 50° C. for 9 hours. The reaction mixture was left to cool to room temperature. In the reaction mixture were added 80 ml of ethyl acetate and saturated sodium chloride aqueous solution, and separated. The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 30 mg of the pyridone compound of the formula (G):

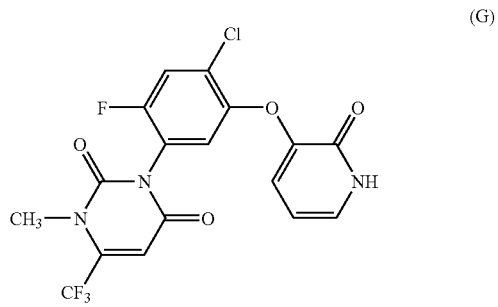

¹H-NMR (395.75M Hz, CDCl₃) δ (ppm): 3.52 (s, 3H), 6.21 (t, J=6.9 Hz, 1H), 6.31 (s, 1H), 6.95 (s, 1H), 7.00 (dd, J=7.3, 1.5 Hz, 1H), 7.26 (dd, J=6.5, 1.7 Hz, 1H), 7.38 (d, J=9.1 Hz, 1H), 13.4 (brs, 1H)

PRODUCTION EXAMPLE 3

Under nitrogen atmosphere, 100 mg of the amide compound of the formula (F) and 49 mg of 1,1,3,3-tetramethoxypropane was added into 1.4 g of polyphosphoric acid, and stirred at 100° C. for 3 hours. The reaction mixture was left to cool to room temperature. In the reaction mixture were added 150 ml of ethyl acetate and 10 ml of saturated sodium chloride aqueous solution, and separated. The organic layer was washed once with 50 ml of saturated sodium chloride aqueous solution, twice with 50 ml of saturated sodium bicarbonate aqueous solution, and once with 35 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 38 mg of the pyridone compound of the formula (G).

PRODUCTION EXAMPLE 4

Under nitrogen atmosphere, 101 mg of the amide compound of the formula (F) and 38 mg of 1,1,3,3-tetramethoxypropane was added into 2 ml of trifluoroacetic acid, and stirred at 70° C. for 9 hours. In this period, 38 mg of 1,1,3,3-tetramethoxypropane was added every 1.5 hour (the total amount of 1,1,3,3-tetramethoxypropane was 228 mg). The reaction mixture was left to cool to room temperature. In the reaction mixture were added 80 ml of ethyl acetate and 30 ml of saturated sodium chloride aqueous solution, and separated. The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 44 mg of the pyridone compound of the formula (G).

PRODUCTION EXAMPLE 5

Under nitrogen atmosphere, 102 mg of the amide compound of the formula (F) and 50 mg of 1,1,3,3-tetramethoxypropane was added into 2 ml of 12.5% hydrogen bromide in acetic acid, and stirred at 50° C. for 2 hours and at 80° C. for 4 hours. The reaction mixture was cooled to room temperature. In the reaction mixture were added 80 ml of ethyl acetate and 30 ml of saturated sodium chloride aqueous solution, and separated. The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 96 mg of the pyridone compound of the formula (G).

PRODUCTION EXAMPLE 6

Under nitrogen atmosphere, 103 mg of the amide compound of the formula (F) and 50 mg of 1,1,3,3-tetramethoxypropane was added into 1 ml of 48% hydrobromic acid, and stirred at 80° C. for 4 hours. The reaction mixture was cooled to room temperature. In the reaction mixture were added 80 ml of ethyl acetate and 30 ml of saturated sodium chloride aqueous solution, and separated. The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 31 mg of the pyridone compound of the formula (G).

PRODUCTION EXAMPLE 7

Under nitrogen atmosphere, 104 mg of the amide compound of the formula (F) and 51 mg of 1,1,3,3-tetramethoxypropane was added into 2 ml of 1 mol/l hydrogen chloride in acetic acid, and stirred at 80° C. for 1.5 hours and at 100° C. for 6 hours. The reaction mixture was cooled to room temperature. In the reaction mixture were added 80 ml of ethyl acetate and 30 ml of saturated sodium chloride aqueous solution, and separated. The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 34 mg of the pyridone compound of the formula (G).

PRODUCTION EXAMPLE 8

Under nitrogen atmosphere, 109 mg of the amide compound of the formula (F) and 53 mg of 1,1,3,3-tetramethoxypropane was added into 0.89 g of trichloroacetic acid, and stirred at 100° C. for 6 hours. The reaction mixture was cooled to room temperature. In the reaction mixture were added 80 ml of ethyl acetate and 30 ml of saturated sodium chloride aqueous solution, and separated. The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 24 mg of the pyridone compound of the formula (G).

PRODUCTION EXAMPLE 9

Under nitrogen atmosphere, 119 mg of the amide compound of the formula (F) and 34 mg of 3-methoxypropenal was added into 2 ml of 12.5% hydrogen bromide solution in acetic acid, and stirred at 80° C. for 2 hours. The reaction mixture was left to cool to room temperature. In the reaction mixture were added 80 ml of ethyl acetate and 30 ml of saturated sodium chloride aqueous solution, and separated. The organic layer was washed once with 30 ml of saturated sodium chloride aqueous solution, twice with 20 ml of saturated sodium bicarbonate aqueous solution, and once with 30 ml of saturated sodium chloride aqueous solution sequentially; dried over anhydrous magnesium sulfate; and concentrated. The residue was subjected to silica gel column chromatography (eluent: methanol/ethyl acetate=5/95) to obtain 100 mg of the pyridone compound of the formula (G).

PRODUCTION EXAMPLE 10

Under nitrogen atmosphere, a mixture of 117 parts of the amide compound of the formula (F), 57 parts of 1,1,3,3-tetramethoxypropane and 211 parts of acetic acid was added into 628 parts of 30% hydrogen bromide in acetic acid which was previously cooled to 10 to 15° C., and stirred at 50° C. for 8 hours. The reaction mixture was cooled to room temperature, and concentrated to the weight of 240 parts under reduced pressure. The mixture of the residue and 69 parts of methanol was added dropwise into the mixture of 1160 parts of ice water and 316 parts of methanol at 0 to 3°

C. The pH of the mixture was adjusted to 7.3 with 40% sodium hydroxide aqueous solution and saturated sodium bicarbonate aqueous solution. The mixture was stirred for half a day being warmed to room temperature, and then filtered off. The filter cake was washed three times with 240 parts of water, and dried under reduced pressure. To the dry cake was added 343 parts of methanol, stirred for 1 hour heating under reflux condition, cooled to room temperature, and filtered off. The filter cake was washed with 114 parts of methanol, and dried under reduced pressure to obtain 96 parts of the pyridone compound of the formula (G) (content: 94%).

PRODUCTION EXAMPLE 11

Under nitrogen atmosphere, a mixture of 48 parts of the compound of the formula (F), 21 parts of 1,1,3,3-tetramethoxypropane, 36 parts of sulfuric acid and 1037 parts of chlorobenzene was stirred at 80° C. for 1 hour. The reaction mixture was cooled to room temperature. In the reaction mixture were added 2250 parts of ethyl acetate and 2500 parts of ice water, and separated. The organic layer was washed twice with 1200 parts of water, once with 1200 parts of saturated sodium bicarbonate aqueous solution, and once with 1200 parts of saturated sodium chloride aqueous solution sequentially; dried over anhydrous sodium sulfate; and concentrated. The residue was subjected to silica gel column chromatography (eluent: methanol/ethyl acetate=5/95) to obtain 32 parts of the pyridone compound of the formula (G).

PRODUCTION EXAMPLE 12

Under nitrogen atmosphere, a mixture of 96 parts of the amide compound of the formula (F), 42 parts of 1,1,3,3-tetramethoxypropane, 49 parts of sulfuric acid and 1618 parts of toluene was stirred at 60° C. for 3 hour. The reaction mixture was cooled to room temperature. In the reaction mixture were added 2250 parts of ethyl acetate and 2500 parts of ice water, and separated. The organic layer was washed twice with 1200 parts of water, once with 1200 parts of saturated sodium bicarbonate aqueous solution, and once with 1200 parts of saturated sodium chloride aqueous solution sequentially; dried over anhydrous sodium sulfate; and concentrated. The residue was subjected to silica gel column chromatography (eluent: methanol/ethyl acetate=5/95) to obtain 65 parts of the pyridone compound of the formula (G).

PRODUCTION EXAMPLE 13

Under nitrogen atmosphere, a mixture of 48 parts of the amide compound of the formula (F), 21 parts of 1,1,3,3-tetramethoxypropane, 33 parts of methanesulfonic acid and 1037 parts of chlorobenzene was stirred at 80° C. for 1 hour. The reaction mixture was cooled to room temperature. In the reaction mixture were added 2250 parts of ethyl acetate and 2500 parts of ice water, and separated. The organic layer was washed twice with 1200 parts of water, once with 1200 parts of saturated sodium bicarbonate aqueous solution, and once with 1200 parts of saturated sodium chloride aqueous solution sequentially; dried over anhydrous sodium sulfate; and concentrated. The residue was subjected to silica gel column chromatography (eluent: methanol/ethyl acetate=5/95) to obtain 34 parts of the pyridone compound of the formula (G).

PRODUCTION EXAMPLE 14

Under nitrogen atmosphere, a mixture of 112 parts of the amide compound of the formula (F), 49 parts of 1,1,3,3-tetramethoxypropane, 78 parts of methanesulfonic acid and 1894 parts of toluene was stirred at 80° C. for 2 hour. The reaction mixture was cooled to room temperature. In the reaction mixture were added 2250 parts of ethyl acetate and 2500 parts of ice water, and separated. The organic layer was washed twice with 1200 parts of water, once with 1200 parts of saturated sodium bicarbonate aqueous solution, and once with 1200 parts of saturated sodium chloride aqueous solution sequentially; dried over anhydrous sodium sulfate; and concentrated. The residue was subjected to silica gel column chromatography (eluent: methanol/ethyl acetate=5/95) to obtain 85 parts of the pyridone compound of the formula (G).

PRODUCTION EXAMPLE 15

Under nitrogen atmosphere, a mixture of 96 parts of the amide compound of the formula (F), 42 parts of 1,1,3,3-tetramethoxypropane, 55 parts of chlorosulfonic acid and 746 parts of chloroform was stirred at 60° C. for 2.5 hours. The reaction mixture was cooled to room temperature. In the reaction mixture were added 2255 parts of ethyl acetate, 500 parts of ice water and 1200 parts of saturated sodium bicarbonate aqueous solution, and separated. The organic layer was washed twice with 1200 parts of water, once with 1200 parts of saturated sodium bicarbonate aqueous solution, and once with 1200 parts of saturated sodium chloride aqueous solution sequentially; dried over anhydrous sodium sulfate; and concentrated. The residue was subjected to silica gel column chromatography (eluent: methanol/ethyl acetate=5/95) to obtain 73 parts of the pyridone compound of the formula (G).

PRODUCTION EXAMPLE 16

Under nitrogen atmosphere, a mixture of 96 parts of the amide compound of the formula (F), 42 parts of 1,1,3,3-tetramethoxypropane, 81 parts of chlorosulfonic acid and 2070 parts of chlorobenzene was stirred at 80° C. for 2 hour. The reaction mixture was cooled to room temperature. In the reaction mixture were added 2250 parts of ethyl acetate and 2500 parts of ice water, and separated. The organic layer was washed twice with 1200 parts of water, once with 1200 parts of saturated sodium bicarbonate aqueous solution, and once with 1200 parts of saturated sodium chloride aqueous solution sequentially; dried over anhydrous sodium sulfate; and concentrated. The residue was subjected to silica gel column chromatography (eluent: methanol/ethyl acetate=5/95) to obtain 73 parts of the pyridone compound of the formula (G).

PRODUCTION EXAMPLE 17

Under nitrogen atmosphere, a mixture of 48 parts of the amide compound of the formula (F), 21 parts of 1,1,3,3-tetramethoxypropane, 41 parts of p-toluenesulfonic acid mono-hydrate and 1037 parts of chlorobenzene was stirred at 80° C. for 2 hour. The reaction mixture was cooled to room temperature. In the reaction mixture were added 2250 parts of ethyl acetate and 2500 parts of ice water, and separated. The organic layer was washed twice with 1200 parts of water, once with 1200 parts of saturated sodium bicarbonate aqueous solution, and once with 1200 parts of saturated sodium chloride aqueous solution sequentially; dried over anhydrous sodium sulfate; and concentrated. The residue was subjected to silica gel column chromatography (eluent: methanol/ethyl acetate=5/95) to obtain 32 parts of the pyridone compound of the formula (G).

Next, the process for producing the starting compound used in the above Production Example will be illustrated as Reference Production Example.

REFERENCE PRODUCTION EXAMPLE 1

Under nitrogen atmosphere, 1.57 g of 2-chloro-3-oxobutylamide, 1.08 g of phenol and 1.7 ml of triethylamine were added into 20 ml of N,N-dimethylformamide, and stirred at 80° C. for 6 hours and at 100° C. for 4 hours. The reaction mixture was left to cool to room temperature. In the reaction mixture were added 100 ml of ethyl acetate and 30 ml of saturated sodium chloride aqueous solution, and separated. The organic layer was washed once with 20 ml of saturated sodium chloride aqueous solution, twice with 20 ml of hydrochloric acid (1 mol/l), and once with 20 ml of saturated sodium chloride aqueous solution sequentially; dried over anhydrous magnesium sulfate; and concentrated. The residue was subjected to silica gel column chromatography (eluent: hexane/ethyl acetate=6/4) to obtain 0.44 g of 3-oxo-2-phenoxybutylamide.

3-Oxo-2-phenoxybutylamide

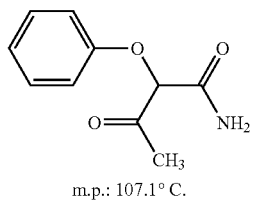

m.p.: 107.1° C.

REFERENCE PRODUCTION EXAMPLE 2

Under nitrogen atmosphere, 8.92 g of 2-chloro-3-oxobutanamide, 20.3 g of the compound of the formula (H):

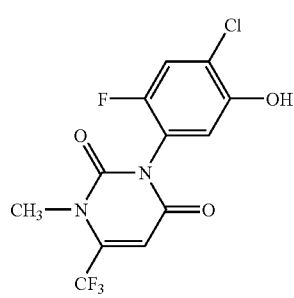

and 16.7 ml of triethylamine were added into 120 ml of N,N-dimethylformamide, and stirred at 70° C. for 1 hour and 100° C. for 4.5 hours. The reaction mixture was left to cool to room temperature. In the reaction mixture were added 200 ml of ethyl acetate and 30 ml of saturated sodium chloride aqueous solution, and the mixture was separated. The organic layer was washed once with 30 ml of saturated sodium chloride aqueous solution, twice with 30 ml of hydrochloric acid (1 mol/l), and once with 30 ml of saturated sodium chloride aqueous solution sequentially; dried over anhydrous magnesium sulfate; and concentrated. The residue was subjected to silica gel column chromatography (eluent: hexane/ethyl acetate=6/4) to obtain 17.9 g of the compound of the formula (F).

The Compound of the Formula (F)

m.p.: 192.3° C.

Next, the process for producing the herbicidal compound by using the compound of the formula (G) obtained the above Production Example as a starting compound will be illustrated as Reference Production Example.

REFERENCE PRODUCTION EXAMPLE 3

Into 15 ml of dichloroethane were added 0.5 g of the compound of the formula (G) and 8 mg of rhodium (II) trifluoroacetate dimmer, and 0.15 g of methyl diazoacetate was added dropwise at 80° C. over 3 hours. After the addition, the mixture was stirred at 80° C. for 1 hour, and concentrated. The residue was subjected to silica gel column chromatography (eluent: hexane/ethyl acetate=3/1 to 0/1) to obtain 0.18 g of the unreacted starting compound of the formula (G) and 0.34 g of 3-(2-chloro-4-fluoro-5-[3-methyl-2,6-dioxo-4-(trifluoromethyl)-1,2,3,6-tetrahydropyrimidine)-2-(methoxycarbonylmethoxy)pyridine:

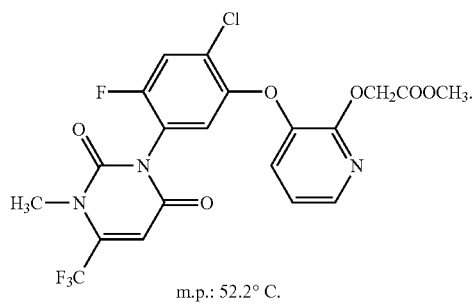

m.p.: 52.2° C.

$^1$H-NMR (300M Hz, CDCl$_3$, TMS δ (ppm)): 3.50 (3H, q, J=1.0 Hz), 3.70 (3H, s), 4.90 (1H, d, J=15.8 Hz), 4.97 (1H, d, J=15.8 Hz), 6.29 (1H, s), 6.90–6.95 (2H, m), 7.32 (1H, dd, J=1.9 Hz, 7.7 Hz), 7.37 (1H, d, J=8.7 Hz), 7.92 (1H, dd, J=1.9 Hz, 4.9 Hz)

INDUSTRIAL APPLICABILITY

The present pyridone compound can be produced from the present amide compound by the present process.

The invention claimed is:

1. The process for producing a pyridone compound of the formula (2):

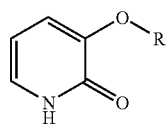

(2)

wherein R is defined below;

which comprises making an amide compound of the formula (1):

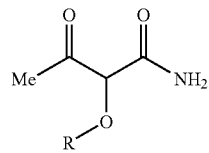
(1)

wherein R represents an optionally substituted phenyl;

react with at least one compound selected from the group consisting of 3-alkoxypropenal of the formula (3), 3,3-dialkoxypropanal of the formula (4), 1,3,3-trialkoxy-1-propene of the formula (5), 1,1,3,3-tetraalkoxypropane of the formula (6), and malonaldehyde:

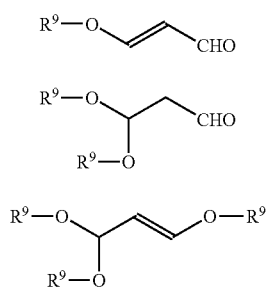
(3)
(4)
(5)

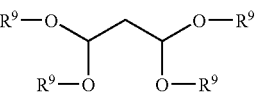
(6)

wherein $R^9$ represents alkyl (e.g. C1–C3 alkyl such as methoxy, ethoxy and the like);

in the presence of a protonic acid.

2. The process according to claim 1, wherein the at least one compound is the 3-alkoxypropenal of the formula (3) or the 1,1,3,3-tetraalkoxypropane of the formula (6).

3. The process according to claim 1, wherein the at least one compound is the 3-methoxypropenal or 1,1,3,3-tetramethoxypropane.

4. The process according to claim 1, wherein the protonic acid is hydrogen halide, phosphoric acid, polyphosphoric acid, sulfuric acid, trihaloacetic acid, or sulfonic acid.

5. The process according to claim 1, wherein the R, in the amide compound of the formula (1) and the pyridone compound of the formula (2), is the radical of the following formula:

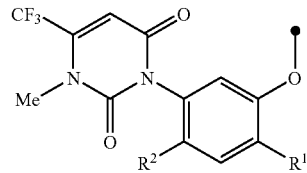

wherein $R^1$ represents a halogen atom or nitro, and $R^2$ represents a hydrogen or halogen atom.

* * * * *